United States Patent
Beer et al.

(10) Patent No.: US 7,244,434 B2
(45) Date of Patent: Jul. 17, 2007

(54) REPLICONS OF PESTVIRUSES THAT DO NOT EXPRESS C AND OR E1 PROTEIN AND INFECTIOUS VIRAL PARTICLES CONTAINING SAME, THAT CAN BE USED IN VACCINES

(75) Inventors: Martin Beer, Neuenkirchen (DE); Ilona Reimann, Gristow (DE)

(73) Assignee: Intervet International B.V., Boxmeer (NL)

( * ) Notice: Subject to any disclaimer, the term of this patent is extended or adjusted under 35 U.S.C. 154(b) by 10 days.

(21) Appl. No.: 10/524,210

(22) PCT Filed: Aug. 12, 2003

(86) PCT No.: PCT/EP03/09031

§ 371 (c)(1),
(2), (4) Date: Feb. 10, 2005

(87) PCT Pub. No.: WO2004/016794

PCT Pub. Date: Feb. 26, 2004

(65) Prior Publication Data

US 2005/0208071 A1    Sep. 22, 2005

(30) Foreign Application Priority Data

Aug. 13, 2002 (EP) .................... 02078357

(51) Int. Cl.
| | |
|---|---|
| A61K 39/12 | (2006.01) |
| A01N 63/00 | (2006.01) |
| C12N 7/00 | (2006.01) |
| C12N 7/04 | (2006.01) |
| C12N 5/00 | (2006.01) |
| C12N 15/86 | (2006.01) |
| C07H 21/04 | (2006.01) |

(52) U.S. Cl. ................ 424/205.1; 424/93.2; 424/93.6; 424/204.1; 424/218.1; 435/235.1; 435/236; 435/325; 435/456; 536/23.72

(58) Field of Classification Search ................ None
See application file for complete search history.

(56) References Cited

U.S. PATENT DOCUMENTS

| 6,180,109 B1 * | 1/2001 | Moormann et al. ...... 424/204.1 |
| 2004/0052818 A1 * | 3/2004 | Heinz et al. ............. 424/202.1 |

FOREIGN PATENT DOCUMENTS

| EP | 1 035 205 A1 | 9/2000 |
| EP | 1 149 901 A1 | 10/2001 |
| WO | WO 01 39801 A2 | 6/2001 |
| WO | WO 2002 066621 A1 | 8/2002 |

OTHER PUBLICATIONS

Widjojoatmodjo M.N. et al.: "Classical swine fever virus Erns deletion mutants: Trans-complementation . . . " J. of Virology (Apr. 2000) V74, N7, p. 2973-2980, XP002227585.

Rumenapf, T. et al.: "Processing of the Envelope Glycoproteins of Pestiviruses" Journal of Virology, Jun. 1993, 67:6, 3288-3294.

* cited by examiner

*Primary Examiner*—Scott D. Priebe
*Assistant Examiner*—Maria Marvich
(74) *Attorney, Agent, or Firm*—Aaron L. Schwartz; William P. Ramey, III (57) ABSTRACT

The present invention provides new Pestiviral RNA genomes (replicons) that are able to replicate, and can be packaged into infectious viral particles in cells that complement the missing protein(s), but do not produce infectious progeny virus. Such replicons can be useful for vaccine purposes.

9 Claims, 5 Drawing Sheets

REPLICONS OF PESTIVIRUSES THAT DO NOT EXPRESS C AND OR E1 PROTEIN AND INFECTIOUS VIRAL PARTICLES CONTAINING SAME, THAT CAN BE USED IN VACCINES

RELATED APPLICATIONS

This application a National Phase filing under 35 U.S.C. §371 of PCT/EP2003/009031 filed on Aug. 12, 2003, claiming priority from EP02078357.7, filed Aug. 13, 2002.

FIELD OF THE INVENTION

The present invention relates to replicons of Pestiviruses that do not express all structural proteins of the virus, infectious viral particles containing said replicons, a method for producing said infectious viral particles and vaccines containing said viral particles.

BACKGROUND OF THE INVENTION

Animals may be protected against pestiviruses by vaccination, however, conventional inactivated or modified live vaccines have disadvantages concerning safety as well as efficacy. Therefore, new types of vaccines should be developed.

Pestiviruses can be divided into two different biotypes, cytopathogenic (cp) and non cytopathogenic (ncp) viruses, respectively. Bovine viral diarrhea virus (BVDV), a member of the genus *Pestivirus* within the family *Flaviviridae* is the causative agent of bovine viral diarrhea, an economically important disease of cattle world-wide. Genetically and structurally closely related virus species are Classical Swine Fever Virus (CSFV) and the ovine Border Disease Virus (BDV). Pestiviruses can induce severe diseases with marked economical losses world wide. The major economic losses caused by BVDV infections are reduced fertility, abortions and the generation of persistently infected calves, which can develop fatal "Mucosal Disease". While cp BVDV induce apoptosis and cell death and express non-structural protein 3 (NS3), inoculation with ncp BVDV leads to persistent infection of cell cultures and NS3-expression is not detectable. The pestivirus genome consists of a single-stranded RNA of positive orientation. The RNA has a length of approximately 12.3 kb and contains one large open reading frame (ORF), which is flanked by non-translated regions (NTR) at both genome ends. The pestiviral ORF is translated into one polyprotein, which is co- and post-translationally processed into 11 (ncp BVDV) or 12 (cp BVDV) mature proteins by viral and cellular proteases. Pestivirus virions consist of four structural proteins, a capsid (C) protein and three glycosylated envelope proteins ($E^{RNS}$, E1, E2). BVDV antibodies are directed against $E^{RNS}$, E2 and NS3. Neutralizing activity was predominantly demonstrated for E2-specific antibodies.

Studies on the replication of pestiviruses have been considerably facilitated by reverse genetic systems and the discovery of autonomously replicating subgenomic RNAs (replicons) (4, 26).

Pestivirus genomes with deletions were first described as defective interfering particles (DI) for BVDV and CSFV (24, 27).

Since then many reports relating to the replication of pestiviruses have been published. Trans-complementation of structural proteins of viruses of the family *Flaviviridae* has been reported.

Pestivirus self-replicating RNAs are important tools for an understanding of virus replication, assembly and egress. Trans-complementation of deleted parts of the genome can be used, for example, for the identification of trans-acting elements of a pestiviral genome.

The minimal requirements for CSFV replication were investigated, for example, by creating defective CSFV genomes lacking the gene sequences for the structural proteins. It was found that the defective CSFV genomes still replicated and could be packaged into viral particles when introduced in SK-6 cells together with helper A187-CAT RNA (Moser et al., J. Virol., 7787-7794, 1999). An autonomously replicating defective BVDV genome which lacks the genes encoding C, $E^{ms}$, E1, E2, p7 and NS2 had been described (Behrens et al., J. Virol., 72, 2364-2372, 1998). For the Kunjin virus (KUN) replicons with deletions in the structural regions were packaged into virons using a system where BHK-21 cells were transfected by two consecutive electropoartions, first with the mutated KUN replicons, and subsequently with a recombinant Semlike Forest Virus replicon expressing KUN structural proteins (Khromykh et al., J. Virol., 72(7), 5967-5977, 1998). For CSFV it had been recognized that trans-complemented defective virions that contained $E^{ms}$ deleted replicons could potentially serve as a basis for vaccines. CSFV, $E^{RNS}$-deleted replicons were generated and trans-complemented using a swine kidney cell line (SK6) constitutively expressing CSFV $E^{RNS}$. The resulting virions were able to infect SK6 cells without the production of infectious virus progeny and could be passaged on $E^{RNS}$-expressing SK6 cells. Pigs were protected against lethal CSFV challenge after immunization with the complemented virions (40).

So far, there are only few reports concerning trans-complementation of BVDV replicons. Defects in the coding regions for non-structural proteins NS3, NSNS4a, NS4B and NS5B were found to be non complementable, whereas defects in the NS5A unit could be complemented in trans (Grassmann et al., J. Virol., 75, 7791-7802, 2001). (4, 18, 36) Trans-complementation of BVDV E2 and/or p7, using cell lines constitutively expressing BVDV E2 and/or p7 for complementation have also been described (Harada et al., J. Virol., 74, 9498-9506, 2000).

SUMMARY OF THE INVENTION

The present invention provides new Pestiviral RNA genomes (replicons) that are able to replicate, and can be packaged into infectious viral particles in cells that complement the missing protein(s), but do not produce infectious progeny virus. Such replicons can be useful for vaccine purposes.

Although it was known in the art that all the genes encoding structural proteins of a Pestivurs can be deleted without affecting the ability to replicate (Behrens et al, supra), such a mutant, missing all structural proteins would not be suitable for vaccine purposes. A vaccine mainly aims at invoking an immune response. A vaccine, on the one hand, should be able to elicit a protective immune response, while, on the other hand, it should of course not invoke the (viral) disease in the inoculated animal or contact animals. The immune response induced is usually mainly directed against the envelop proteins of the virus. But, if a replicon would be used from which all the structural, more particular, all the envelop protein coding sequences have been deleted, such proteins would not be produced from the replicon and no immune response to these proteins would be obtained.

The present inventors aimed at providing a replicon that would still encode most, preferably all, envelop proteins of the virus, while, on the other hand, it would not be capable of producing infectious progeny virus.

The present invention provides a replicon of a Pestivirus, preferably the Bovine Viral Diarrhea Virus (BVDV), which expresses all structural proteins of BVDV except for a functional C and/or E1 protein. Preferably at least part of the coding sequence of the E1 or C protein has been deleted from said replicon.

DETAILED DESCRIPTION OF THE INVENTION

A replicon is a self-replicating RNA molecule. In this case the RNA molecule is the RNA genome of the BVD virus. Replicons can be constructed from a full length c-DNA clone of the BVD virus, for example from a full-length BVDV cDNA clone like pA/BVD/ins- (Meyers et al., J. Virol. 70:8606-8613, 1996). The BVDV RNA contains one ORF that is translated into one polyprotein, which is processed into mature proteins by viral and cellular proteases. In constructing mutated replicons care should be taken not to introduce a frameshift within the BVDV ORF. Furthermore, when coding sequences for structural proteins are deleted, the sequences encoding some N and/or C terminal amino acids may be retained to ensure proper post translational processing of the precursor polypeptide (protease cleavage sites are retained), For example, the capsid (C protein) of BVDV strain NCP7 is encoded by amino acids (AA) 169-270. About 25 amino acids at the C terminus (M245270) function as a signal sequence for the translocation of the $E^{RNS}E1E2$ polyprotein, and as a putative anchor of the capsid protein. The signal sequence at the C terminus of the capsid protein is essential for a further processing of the polyprotein downstream.

In case where expression of a functional C protein is prevented by deleting part of the gene encoding the C protein, the coding sequence encoding the part of the protein essential for further downstream processing should preferably be retained. For the C protein a about 32 AA should preferably be retained at the N terminus. The exact length of the sequences necessary for downstream processing may vary per strain or cell type.

The envelop protein E1 of BVDV strain NCP7 is encoded by amino acids 498 to 692. About 33 amino acids at the C terminus (AA 660 to 692) function as a signal sequence for the translocation of the E2 envelop protein, and as a putative anchor of the E1 envelope protein.

However, other signal sequences or the analogous sequences of other pestivirus species (e.g. CSFV) may be used instead of, for example, the BVDV sequence. For E1 mutants of BVDV no M at the N terminus have any function as a signal sequence.

For both E1 and C mutants several ways for construction of replicons are conceivable, that do not express the functional proteins. For example, such mutations may be created by partial deletions whereby the signal sequences are retained, or partial or complete deletions whereby the signal sequences are replaced by analogous signal sequences, or mutations where only base pair exchanges are made.

The present inventors proved for the first time, that both C and E1 structural proteins are essential for the formation of infectious pestiviruses. Furthermore it was shown that deletion of C and E1 does not impact the ability of RNA self-replication.

By using cell lines constitutively expressing Pestiviral structural proteins, Capsid- or E1-proteins can be efficiently trans-complemented. The resulting virions are able to infect target cells and to transfer the replicons without generating infectious replication-competent virus progeny. The complemented virions are indistinguishable from wild-type Pestivirus in virus neutralization experiments and can be completely neutralized by, for example in the case of BVDV, a BVDV-specific serum as well as by a BVDV E2-specific serum. Recombinations yielding infectious wild-type BVDV were not detected in any of the complementation experiments.

The complemented viruses may be used for the safe and efficacious immunization against a Pestivirus, such as BVDV.

Infection of cells and animals with the trans-complemented viruses results in replicating RNAs expressing all encoded proteins in the infected cells but which do not generate viral particles.

Thus the complemented virions can be used for the immunization against an infection with a pestivirus, such as BVDV, and can protect vaccinated animals from Pestivirus-related disease.

In a preferred embodiment a replicon according to the invention does not encode a functional C protein. This can be achieved by deleting at least part of the coding sequence for the C protein. In case of BVDV, preferably the coding region encoding amino acid positions 201-243 of the C protein is deleted.

In another embodiment of the present invention the replicon does not encode a functional E1 protein. For BVDV, preferably the coding region encoding amino acid positions 498 to 653 of the E1 protein are deleted.

It has been found that the C protein, which is the capsid protein of the virus, as well as the E1 protein, is essential for obtaining infectious virus. Mutants that lack the coding sequence for the C or the E1 protein are thus not infectious. The advantage of mutants that do not encode a capsid or E1 protein, but do encode all (envelop) proteins responsible for the immune response (especially E2 and $E^{ms}$) is that the immune response will still include a response against all envelop proteins, since the coding sequences for all envelop proteins is still present.

Likewise part of the present invention are infectious viral particles of a pestivirus that contain a replicon according to the invention. Such particles can be incorporated in a vaccine for said Pestivirus, for example BVDV.

A method for the production of viral particles according to the invention is likewise part of the invention. Such a method may comprise the following steps:

a. Providing cells that are permissive for a particular Pestivirus (for example BVDV) and express a Pestiviral E1 and/or C protein,
b. Transfecting said cells with a replicon according to the invention,
c. Culturing transfected cells obtained in step b,
d. Harvesting the viral particles from the cell culture.

Preferably the particles produced in step d are used to infect fresh cells that are permissive for a particular Pestivirus (for example BVDV) and express a Pestiviral E1 and/or C protein again.

Cells that can be used in the production of the viral particles according to the invention should at least be capable of expressing the C protein and/or the E1 protein of a pestivirus, which may the pestivirus on which the replicon is based or another Pestivirus. In case of BVDV said cells should preferably express the E1 and or C protein of BVDV. Examples of suitable complementing cell lines are disclosed in the Examples.

In case of BVDV, such cells are preferably of bovine origin, for example bovine kidney cells or diploid bovine esophageal cell line.

The ways by which the coding sequences of a pestivirus such as BVDV can be introduced into said cells are known in the art. For example, the coding sequences for the structural proteins of BVDV (at least C and/or E1) may be introduced into said cells by way of an expression plasmid encoding said proteins or by way of a helper virus. When the viral particles are intended to be used in a vaccine the use of expression plasmids is preferred, to avoid complicated purification methods due to the presence of a helper virus. Suitable expression plasmids are known in the art. After transfection of replicon RNA infectious viral particles are produced. The cells can be grown according to methods known in the art until the desired viral titer is obtained. Virus may be harvested from the supernatant of the cell culture or from total cell lysates.

Methods used to transfect the cells and the various cloning procedures are known in the art (for example: Sambrock, J & Russel, D. W. Molecular Cloning: A laboratory Manual (Cold Spring Harbor Press, New York, 2001). All permanent cell lines which are suitable for the replication of pestiviruses may be used, preferentially cells of bovine origin. Preferably cells are used that can be easily transfected with DNA. The coding sequences of the structural proteins of most of the pestiviruses contain cryptic splicing sites. Therefore, for most of the BVDV strains, a synthetic open reading frame (synORF) eliminating the splicing sites may be constructed to ensure expression with promoters using the nuclear pathway (e.g. HCMV promoter). However other expression systems (viruses, replicons from other viruses, pestivirus replicons with different deletions) may provide the deleted proteins for trans complementation.

A vaccine containing infectious viral particles according to the invention together with a pharmaceutically acceptable carrier is likewise part of the present invention.

BRIEF DESCRIPTION OF THE FIGURES

FIG. 1.

Schematic representation of the generated constructs. Filled boxes represent the BVDV structural region. Dotted lines show the deleted regions and numbers indicate the nucleotide position in the BVDV full-length RNA. Arrows indicate restriction enzyme sites flanking the deletions. Lines at the left and right ends indicate untranslated regions. $N^{pro}$, autoprotease; C, capsid protein; $E^{RNS}$, E1 and E2, envelope proteins; p7, nonstructural protein; N2 to NS5, nonstructural proteins, 3'-UTR and 5'-UTR, noncoding regions. The scale in kb is given.

FIG. 2:

Detection of BVDV-specific antibodies after immunization with NCP7_ΔC_trans and challenge infection with BVDV type 1 using an indirect ELISA system (A), and an NS3-blocking-ELISA (B). Mean values of the animal groups are shown. Neutralizing titers at day 62 p. immunization are 1:256 or higher.

FIG. 3:

Detection of BVDV-specific neutralizing antibody titers after immunization with NCP7_ΔC_trans. Mean values of the animal groups are shown.

FIG. 4:

Relative leukocyte counts and body temperatures after challenge infection (mean values)

FIG. 5:

Detection of BVDV ERNS antigen with a commercial ELISA system (Checkit BVD Virus III, Dr. Bommeli AG). Mean values of the animal groups are shown.

EXAMPLES

Example 1

Construction and Characterization of BVDV Replicons

Figure 1:
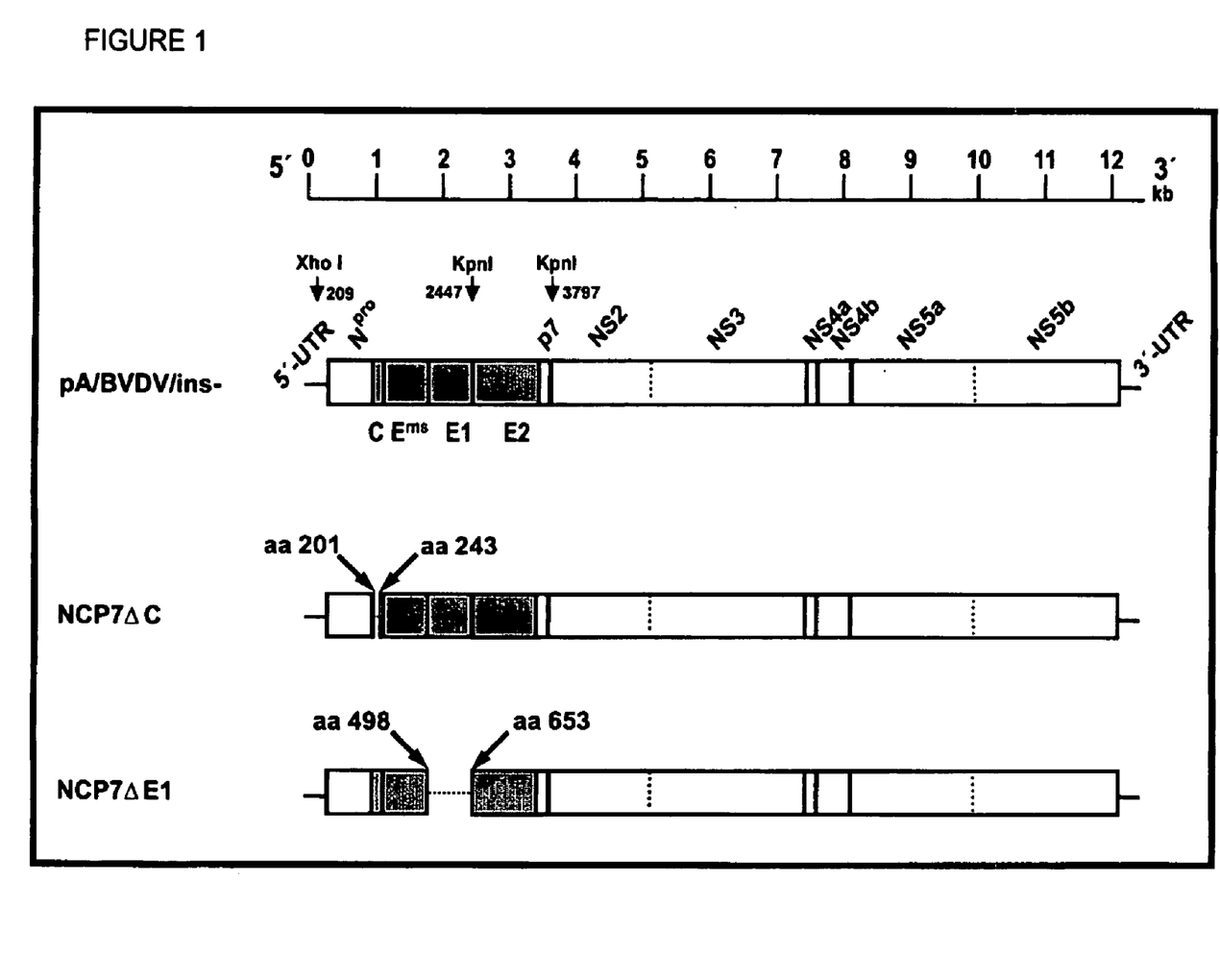

After establishment of an infectious clone for BVDV CP7, a variant of the construct with a deletion of a 27 nucleotide insertion was generated that allowed recovery of ncp BVDV (26). Based on this construct termed pA/BVDV/Ins-, replicons were constructed by deletion of sequences encoding C and E1 (FIG. 1) without introducing a frameshift within the BVDV ORF. Mutant BVDV clones shown in FIG. 1 were constructed on the basis of the full-length cDNA clone pA/BVDV/ins-. Location of restriction sites are indicated by superscript numbers corresponding to their cleavage positions in the BVDV/CP7 genome (FIG. 1).

Plasmid Constructs

The NCP7ΔC and NCP7ΔE1 plasmids were constructed by a two step cloning procedure. Two PCR fragments were inserted into plasmid pA/BVDV/ins- digested with $XhoI^{209}$ and $KpnI^{2447,3797}$ (Tab. 1).

Plasmids were amplified in *E. coli* TOP10F' cells (Invitrogen). Restriction enzyme digestion and cloning procedures were performed according to standard protocols. Plasmid DNA was purified by QIAGEN Plasmid Mini, Midi or Maxi kits.

The primers used for PCR or sequencing (labeled with IRD 800) were custom synthesized (MWG-Biotech). Primer pairs for generation of the respective constructs are summarized in Table 1.

The resulting replicons contained a deletion of a part of the Capsid region (NCP7ΔC, amino acids position 201 to 243 (FIG. 1) or of the E1 encoding region (NCP7ΔE1, amino acid position 498 to 653 (FIG. 1).

All deletions were confirmed by PCR and nucleotide sequencing of the resulting cDNA clones.

Polymerase Chain Reaction (PCR) and Sequencing

For PCR, a PTC-200 thermal cycler (MJ Research, Inc.) was used. DNA based amplification was done by Expand High Fidelity PCR System (Roche Molecular Biochemicals) according to the supplier's protocol. For RT-PCR, total RNA of virus-infected cells was extracted using the TRIZOL reagent (Gibco-Life Technologies).

cDNA was amplified from the RNA template by using reverse transcriptase (Promega) and a sequence-specific primer. The synthesized cDNA was amplified with a thermostable Taq Polymerase (Promega) and PCR products were directly sequenced. Sequencing was carried out using a Thermo Sequenase Cycle Sequencing Kit (Amersham Biosciences). Nucleotide sequences were read with a LI-COR automatic sequencer (MWG Biotech) and were analyzed using the Wisconsin software package version 9.1 (Genetics Computer Group, USA).

In Vitro-Transcription and Electroporation

Subsequently, in vitro-transcribed full-length replicon RNA was transfected into BVDV-negative PT cells.

In vitro-transcription of linearized full-length cDNA constructs and replicons was performed by T7 RiboMaX™ Large Scale RNA Production System (Promega) according to the manufacturers instructions. The amount of RNA was estimated by ethidiumbromide staining after agarose gel electrophoresis. For transfections, 1×10⁷ PT, PT_805 or KOP-R cells were detached using a trypsine solution, washed with phosphate buffer saline without $Ca^{++}/Mg^{++}$ ($PBS^-$), mixed with 1 to 5 µg of in vitro synthesized RNA and electroporated (two pulses at 850V, 25 µF, 156Ω) using an EasyjecT Plus (EquiBio) transfection unit.

Characterization of the Replicons

For the detection of BVDV proteins, monoclonal antibodies (mab) WB210 (anti-$E^{RNS}$, CVL, Weybridge), WB215 (anti-E2, CVL, Weybridge), CA3 (anti-E2, Institute for Virology, TiHo Hannover), mab-mix WB103/105 (anti-NS3, CVL, Weybridge), and C16 (anti-NS3, Institute for Virology, TiHo, Hannover) were used (15, 16, 31).

Transient expression of NS3 could be detected from 24 h post transfection by IF for all replicons. Additionally, also $E^{RNS}$- and E2-specific immunofluorescence was demonstrated. However, no infectious recombinant BVDV could be recovered, even after serial passages and co-passages using highly susceptible KOP-R cells (Table 2). The intensity of NS3-specific immunostaining of NCP7ΔC and NCP7ΔE1-transfected PT cells was comparable to cells transfected with full-length NCP7 RNA and more than 85% of the cells were positive in IF (Table 2). Transfection of full-length NCP7 RNA into PT cells resulted in virus titers of up to 10³ IU/ml. As expected, electroporation of cells with RNA of the prototype replicon DI9 (4) did not lead to recovery of infectious BVDV, but a strong immunofluorescence following NS3 staining was observed. RT-PCR of PT cells transfected with replicons or full-length NCP7 demonstrated presence of BVDV-specific RNA of the expected size containing the correct deletions. In summary, deleted BVDV genomes, which were replication-competent but lacked the ability of generating virus progeny, were constructed and could efficiently be transfected into bovine cells.

TABLE 1

Construction of BVDV-replicons

| replicon | deletion (nt) | deletion (aa) | primer | sequence (5'→3') | position (nt) | sense |
|---|---|---|---|---|---|---|
| ncp7ΔC | 969–1095 | 201–243 | cp7-204 | AAGCCTCGAGATGCCACGTGG | 204–224 | + |
| (KpnI²⁴⁴⁷ mutated) | | | C-969R-KpnI | tctaggtaccTCTCTGACTCCTTAGGTGTTATC | 969–947 | − |
| | | | cp7-1096-Kpn | gagaggtaccCTCAAGAGTCGCGCAAGAAAC | 1096–1116 | + |
| | | | p7-3804R | GTCCTAGGTACCCCTGGGCA | 3785–3804 | − |
| ncp7ΔE1 | 1860– | 498–653 | cp7-204 | AAGCCTCGAGATGCCACGTGG | 204–224 | + |
| (KpnI²⁴⁴⁷ mutated) | 2333 | | cp7-1859R-KpnI | tcaggtaccGTGCATATGCCCCAAACCATGTC | 1859–1838 | − |
| | | | cp7-2334-KpnI | caacggtaccGAATTTGGACCGCTGCTACAACC | 2334–2354 | + |
| | | | p7-3804R | GTCCTAGGTACCCCTGGGCA | 3785–3804 | − |

The nucleotides sequences are SEQ ID NO:8; SEQ ID NO:2; SEQ ID NO:3; SEQ ID NO:4; SEQ ID NO:5; SEQ ID NO:6; SEQ ID NO:7; and SEQ ID NO:1, respectively.

TABLE 2

Replication and trans-complementation of BVDV NCP7 RNAs with in-frame deletions (replicons).

| construct | replication[a] after RNA transfection in PT cells (24 h) | 1st passage[b] (24 h, 48 h, 72 h) on KOP-R-cells | Titer of virus progeny[c] 24 h after transfection of complementing PT_805 cells (IU/ml) | 4th passage[d] of virus progeny on KOP-R cells |
|---|---|---|---|---|
| NCP7 | ++(P)[e] | +(10³ IU/ml) | 10⁷·³ (P) | +(P) |
| NCP7ΔC | ++[f] | Ø[f] | >10⁵·⁰ | Ø |
| NCP7ΔE1 | ++ | Ø | >10⁵·⁰ | Ø |
| DI9 | +++ | Ø | <10⁰ | nd |

[a]PT cells were transfected with in vitro-transcribed RNA and IF-stained for NS3-expression after 24 h.
[b]KOP-R cells were inoculated with undiluted supernatants 24 h, 48 h and 72 h after transfection of PT cells (1 ml per 10⁵ cells). KOP-R cells were stained with NS3-specific mabs 5 days post inoculation.
[c]PT_805 cells were transfected with in vitro-transcribed RNA and the supernatants were titrated after 24 h using KOP-R-cells.
[d]KOP-R cells were inoculated using supernatants of transfected PT_805 cells with a titer >10⁶ IU/ml (1 ml per 10⁵ cells).
[e]P indicates the detection of virus plaques after NS3-staining (>10 cells).
[f]Ø = no BVDV-specific immunofluorescence; + = weak positive NS3-IF-signal and <50% IF-positive cells, ++ = positive NS3-IF-signal >50% IF-positive cells, +++ = strong positive NS3-IF-signal and >50% IF-positive cells.
[g]nd = not done

Example 2

Establishment of C-E$^{rns}$-E1-E2 Expressing Cells

Establishment of C-E$^{RNS}$-E1-E2 expressing PT cells

In order to do complementation studies with the BVDV replicons, a bovine cell line was established that constitutively expresses BVDV structural proteins.

PT cells (RIE11 CCVL), a permanent bovine kidney cell line, was obtained from the collection of cell lines in veterinary medicine at the Federal Research Center of Virus diseases of Animals, Insel Riems (CCLV). PT cells were chosen due to their applicability for DNA/RNA transfection and for generation of constitutively expressing cell lines. Cells were grown in Dulbecco's minimal essential medium (DMEM) supplemented with 10% BVDV-free fetal bovine serum (FBS).

The genomic region encoding the structural proteins (C-E$^{RNS}$-E1-E2) of BVDV strain PT810 (41) was cloned as a chemically synthesized synthetic open reading frame (Syn-ORF; kindly provided by Tobias Schlapp, Bayer AG, Leverkusen). It consisted of 2694 nucleotides extending from nucleotide 890 to 3584 of the nucleotide sequence of BVDV strain NADL (9) and was inserted into the pcDNA3.1 expression plasmid (Invitrogen) using restriction sites KpnI and NotI. The nucleotide sequence of Syn-ORF had been changed to remove splice sites (35), but retained the original amino acid sequence of BVDV strain PT810. Additionally, the first codon of Syn-ORF was changed to a methionin to allow expression of the polyprotein under the control of the HCMV immediate early promotor present in pcDNA3.1, and a stop codon was inserted behind the last codon.

The resulting construct pcDNA_C-E2 (1 µg) was used to transfect PT cells with the SUPERFECT reagent (Qiagen). At 2 days after transfection, cell culture medium was changed to DMEM supplemented with 10% bovine serum and 1 mg of G418 (Gibco, Life Technologies) per ml. G418-resistant colonies were isolated, and replated several times.

After G418 selection and passaging, resistant cell clones were tested for BVDV E$^{RNS}$ and E2 expression using mabs WB210 and WB215, respectively. Positive cells were cloned, passaged under G418 selection and tested again for E$_{RNS}$ and E2 expression. In the IF analyses, G418-resistant cell clone PT_805 contained more than 90% E$^{RNS}$ and E2 expressing cells. During further passaging of PT_805 cells for 6 months in the presence of G418, the portion of E$^{RNS}$ and E2 expressing cells remained stable. Immunoprecipitation experiments with E$^{RNS}$- and E2-specific mabs showed a protein pattern identical to that of BVDV infected PT cells, where gylocprotein E1 is co-precipitated with the E2-specific mab (data not shown). From these data and those obtained by nucleotide sequencing it was concluded that all BVDV structural proteins were constitutively expressed in PT_805 cells. The cell line was used for trans-complementation experiments and for the generation of infectious virions as well as for packaging and transducing deleted replicons.

Recovery and Characterization of Trans-Complemented Recombinant BVDV

For trans-complementation experiments, in vitro-transcribed BVDV replicon RNA or full-length NCP7 RNA was transfected into monolayers of PT_805 cells by electroporation. Cell culture supernatants were collected 24 h, 48 h and 72 h post transfection (p.t.), clarified by centrifugation (10,000×g, 5 min) and titrated using highly susceptible KOP-R cells. KOP-R cells (RIE244, CCVL) are cells of a diploid bovine esophageal cell line, obtained from the collection of cell lines in veterinary medicine at the Federal Research Center of Virus diseases of Animals, Insel Riems (CCLV). KOP-R cells were selected due to their susceptibility to BVDV infection and their suitability for BVDV propagation. Cells were grown as described above for the PT cells. As a negative control for replication, replication incompetent controls were used (deletion mutants NCPΔNS5 and NCP7Δ3'ntraatll).

At the day of collection, replication of BVDV was monitored by IF staining.

Virus titers of the complemented viruses were determined as infectious units (IU). Cell culture supernatants were titrated in triplicate in $\log_{10}$ steps and 1 ml was inoculated onto KOP-R cells seeded in 24-well plates. After 12 h of incubation at 37° C., cells were washed, detached with a trypsin solution, and counted. An aliquot of the cells was stained by IF using a BVDV NS3-specific mab and analyzed by flow cytometry. Infectious units (IU) were calculated according to the formula:

number of cells in the well×% IF-positive cells×
dilution factor=titer in IU/ml

For calculations, only wells with >5% and <30% IF-positive cells were considered.

For all replicons and full-length NCP7, NS3 staining following RNA transfection led to immunofluorescence patterns similar to that obtained with PT cells. Between 80% and 95% of transfected cells were reactive with NS3-specific antibodies. Infectious recombinant BVDV was detected in supernatants of NCP7ΔC, NCP7ΔE1 and NCP7-transfected PT 805 cells as shown by infection of KOP-R cells. Virus titers of the resulting complemented viruses NCP7ΔC_trans and NCP7ΔE1_trans varied between $10^{4,0}$ to $10^{6.6}$ IU/ml at 24 h p.t. (Table 2). After transfection of full-length NCP7 RNA into complementing PT_805 cells, virus titers of up to $10^{7.3}$ IU/ml could be detected at 24 p.t. (Table 2). Therefore, titers of trans-complemented viruses from supernatants collected at 24 h p.t. were approximately 10000-fold higher than virus titers obtained after transfection of full-length NCP7 RNA into non complementing PT cells (Table 2). In addition, no complemented BVDV was detected after passaging of PT_805 cell culture supernatants transfected with DI9 replicon RNAs (Behrens et al., J. Virol., 72, 2364-2372, 1998) at all times p.t. (Table 2).

Using IF of KOP-R cells infected with NCP7ΔC_trans and NCP7ΔE1_trans, expression of E$^{RNS}$, E2 and NS3 could be detected (Table 2). Expression pattern indicated that supernatants of transfected PT_805 cells contained infectious virus that can infect and replicate in KOP-R cells. Titration experiments and subsequent IF staining demonstrated that no cell-to-cell spread occurred, and that neither NCP7ΔC_trans nor NCP7ΔE1_trans were able to form NS3-positive plaques or secondary infections in these cells (Table 2). At higher dilutions, only single cells or small foci of cells were positive by IF-staining for NS3. Control experiments with BVDV NCP7 on KOP-R cells resulted in antigen positive virus plaques as demonstrated for E$^{RNS}$, NS3 and E2.

The infection of KOP-R cells with trans-complemented viruses could be blocked with BVDV-neutralizing antisera (S-BVD_pos, S-BVD$_{13}$ E2) and no infectivity was detected after inoculation of KOP-R cells (100% neutralization). For neutralization of BVDV, 100 µl of virus suspension ($10^4$ TCID$_{50}$/ml) was mixed in a 24-well plate with 50 µl of undiluted serum and incubated at 37° C. After 2 h, KOP-R cells (2×10⁴) were transferred to the mixture and incubated for 3 days at 37° C. Subsequently, the monolayer was stained for BVDV-NS3 by indirect immunofluorescence (IF) (19). (S-BVD_pos) was a pooled anti-BVDV serum collected from cattle experimentally infected with BVDV strain PT810 (3). The homologous neutralization titer of this serum was 1:4,096. For E2-specific neutralization, serum from sheep, immunized with an E2-expressing modified Vaccinia Virus Ankara (MVA) was used (S-BVD_E2; Beer et al., unpublished data). In a control reaction, incubation with a BVDV antibody-free cattle serum (S-BVD_neg) did not result in virus neutralization (Table 3).

TABLE 3

Neutralization of wild-type and complemented BVD viruses by BVDV-specific antisera

| | IF analysis 3 days post inoculation of the neutralization mix | | |
|---|---|---|---|
| BVDV[a] | S-BVD_pos[b] | S-BVD_E2[c] | S-BVD_neg[d] |
| NCP7 | Ø | Ø | +[e] |
| NCP7ΔC_trans | Ø | Ø | + |
| NCP7ΔE1_trans | Ø | Ø | + |

[a]Complemented viruses were adjusted to a titer of 10⁴ IU/ml.
[b]Cattle serum prepared against BVDV type 1.
[c]Sheep serum specifically directed against BVDV type 1 E2.
[d]BVDV antibody free cattle serum.
[e]Ø = no IF-positive cells, + = more than 100 IF-positive cells/well.

Example 3

Establishment of C-E$_{RNS}$ Expressing PT Cells (PT 875)

In order to do complementation studies with the BVDV replicons, a bovine cell line was established that constitutively expresses the BVDV structural proteins Capsid and E$^{RNS}$.

The genomic region encoding the structural proteins C and E$^{RNS}$ of BVDV strain PT810 (41) was cloned after PCR amplfication of the C-E$^{RNS}$ sequence from the synthetic ORF (Syn-ORF, nucleotides 17 to 1000; see "Establishment of C-E$^{rns}$-E1-E2 expressing cells") encoding C-E$^{RNS}$-E1-E2. The PCR product was inserted into the pcDNA3.1 expression plasmid (Invitrogen) using restriction sites NotI and XbaI, which had been included into the PCR primers.

The resulting construct pcDNA_C-E$_{RNS}$ (1 µg) was used to transfect PT cells with the SUPERFECT reagent (Qiagen). At 2 days after transfection, cell culture medium was changed to DMEM supplemented with 10% bovine serum and 1 mg of G418 (Gibco, Life Technologies) per ml. G418-resistant colonies were isolated, and replated several times. After G418 selection and passaging, resistant cell clones were tested for BVDV E$^{RNS}$ expression using mab WB210. Positive cells were cloned, passaged under G418 selection and tested again for E$^{RNS}$ expression. In the IF analyses, G418-resistant cell clone PT_875 contained more than 80% E$^{RNS}$ expressing cells. The cell line PT_875 was used for trans-complementation experiments with BVDV replicons with a deletion in the capsid encoding region.

Trans-Complementation of NCP7_ΔC with PT_875 Cells

Transfection with NCP7_ΔC led to immunofluorescence patterns similar to that obtained with PT cells. Between 80% and 95% of transfected cells were reactive with NS3-specific antibodies. Infectious recombinant BVDV was detected in supernatants of NCP7ΔC-transfected PT 875 cells as shown by infection of KOP-R cells. Virus titers of the resulting complemented viruses NCP7ΔC_trans varied between $10^{3,0}$ to $10^5$ IU/ml at 24 h p.t. (data not shown).

Example 4

Immunization of Cattle with Trans-Complemented NCP7ΔC: Data after Immunization

Material and Methods

Trans-complemented NCPΔ7C replicon for immunization (NCP7_ΔC_trans) In vitro-transcribed NCP7_ΔC RNA was transfected into PT_805 helper cells. Helper cell supernatants were collected at 24 and 48 h post transfection, and stored at −70° C. Trans-complemented virions were titrated using KOP-R cells, and titers in IU were determined. Virion preparations used for immunization were tested for bacterial and viral contaminants. In addition, by using passaging on KOP-R cells and RT-PCR analysis, revertant BVDV as well as wild-type BVDV has been excluded.

Animals, Immunization Protocol, Challenge Infection, Sample Collection, and Clinical Observation Ten healthy cattle ("Simmental" breeds) seronegative to BVDV and BHV-1 and aged between 3 to 5 months were used in this experiment. Five animals were vaccinated twice intramuscularly (i.m.) and intranasally (i.n.) 29 days apart. Each animal of the vaccine group (animals no. 173, 537, 554, 758, 977) received 4 ml virus suspension containing $10^6$ IU/ml of NCP7_ΔC_trans (2 ml i.n using an aerosol dispenser adapted to a MUTO™ syringe, and 2 ml i.m.). Five calves were used as unvaccinated controls (animals no. 97, 99, 172, 610, 611). All animals were challenged at day 62 after the first immunization with the wild-type BVDV strain SE5508 (Wolfmeier et al., Arch. Virol., 142, 2049-2057, 1997) using an aerosol dispenser adapted to a MUTO™ syringe. Every animal received 1 ml virus suspension per nostril with a titer of $10^6$ TCID$_{50}$. Nasal swabs and EDTA blood samples were taken daily during the first 10 days after each immunization, and after challenge infection (p. chall.). Additional samples were collected at day 14, 21, and 28 p. imm./p. chall., respectively. Serum samples were collected at days 0, 3, 7, 14, 21, 29 p. imm./p. chall. from all animals.

Total white blood cell counts (WBC) were determined by size distribution analyses with a Cell-Dyn3700 analyser (Abbott). A clinical score including body temperature was determined for 14 days post each immunization, and for 28 days post challenge infection.

Serology

Neutralisation Assay

Sera from all animals were tested in a standard serum neutralisation test (SNT) versus BVDV strains CP7 and SE5508. The sera were inactivated (30 min, 56 CC) and diluted (log$_2$; 50 µl) using cell culture medium (MEM, 10% FBS) in triplicates in 96-well plates. One hundred TCID$_{50}$ BVDV in 50 µl were added and the plates were incubated at 37° C. After 2 hour of incubation, 2×10⁴/well BVDV-negative KOP-R cells in 100 µl cell culture medium were added and the plates were incubated for 5 days at 37° C. and 5% CO$_2$. BVDV antibody-positive and -negative sera were used as controls, and virus titer was confirmed by back-titration (log$_{10}$, n=8). BVDV infection was detected in the cells by indirect immunofluorescence staining. Neutralizing titres were calculated as the geometric mean values of the reciprocal last dilution (n=3) in which no IF signals were observed.

BVDV Antibody ELISAs

The indirect BVDV ANTIBODY ELISA (IDEXX) and the NS3 blocking BVDV ANTIBODY CEDI-TEST (Cedi-Diagnostics) were used to determine BVDV—as well as BVDV NS3-specific antibodies. Both assays were used according to the manufacturers instructions.

Virus Isolation

Virus was isolated by using co-cultivation of blood leukocytes with KOP-R cells or inoculation of nasal swabs on monolayers of KOP-R cells. After an incubation period of 4 to 6 days the cells were analysed for BVDV NS3 by using IF staining.

Virus Isolation from Blood Leukocytes

EDTA blood containing $10^7$ leukocytes was centrifuged after haemolysis, washed twice with ice-cold PBS and re-suspended in 1 ml PBS. KOP-R cell cultures were inoculated using $10^6$ washed leukocytes (n=2) in 100 µl PBS and incubated for 4 to 6 days. BVDV was detected using IF staining with NS3-specific mab.

Virus Isolation from Nasal Swabs

Nasal swabs (about 100 mg secretion/swab) were stabilised in 1 ml PBS containing antibiotics, and 5% BVDV antibody free bovine serum. Following vortexing for 20 sec, an 100 µl aliquot was inoculated on KOP-R cell cultures (n=2). After an incubation period of 4 to 6 days, cells were investigated for BVDV NS3-antigen using IF staining.

$E^{RNS}$ Capture ELISA

For the detection of BVDV antigen after challenge infection, blood samples from all animals were tested with a commercially available $E^{RNS}$ capture ELISA system (Checkit BVDV III, Dr. Bommeli AG, Switzerland) according to the instructions of the manufacturer.

Results

Health Status after Application of NCP7_ΔC_Trans

All animals remained healthy after immunization with NCP7_ΔC_trans, and no abnormal clinical score was observed. Neither leukopenia nor increased body temperatures could be determined (data not shown).

Serology After Immunization

Figure 2:
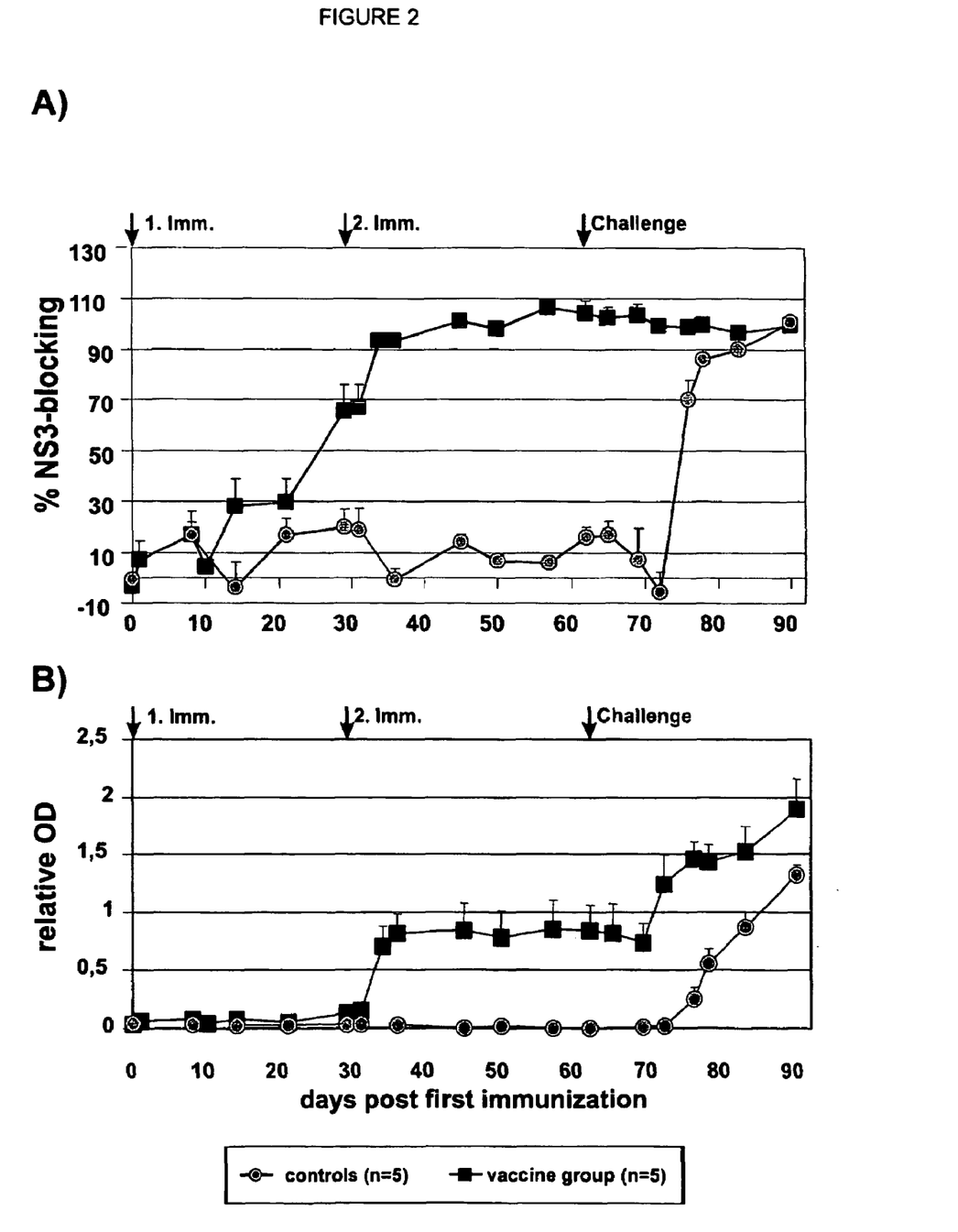

All animals were free of BVDV antibodies at the beginning of the experiment (BVDV antibody ELISAs and neutralization assays versus BVDV type I and II), and all control animals remained BVDV antibody negative until BVDV challenge infection. After the first immunization with NCP7_ΔC_trans all animals of the vaccine group scored positive for NS3-specific antibodies at day 29 p. imm. (mean value: 66%), but were negative in an indirect BVDV ELISA (mean value: 0.13). NS3-specific antibody responses could be detected as early as 14 days p. imm. in sera from vaccinated animals (FIG. 2a). After the first immunization neutralizing antibody titers between 1:3 and 1:12 versus the BVDV strain SE5508 could be detected (FIG. 3).

After the second immunization all immunized animals scored positive in both the NS3 blocking and the indirect ELISA (FIG. 2). Mean ELISA values of about 100% (NS3 blocking ELISA) and about 0.8 (indirect ELISA) could be detected between days 7 and 29 after the second immunization (FIGS. 2a and b). In the indirect ELISA, a clear booster effect could be observed (FIG. 2b).

Figure 3:
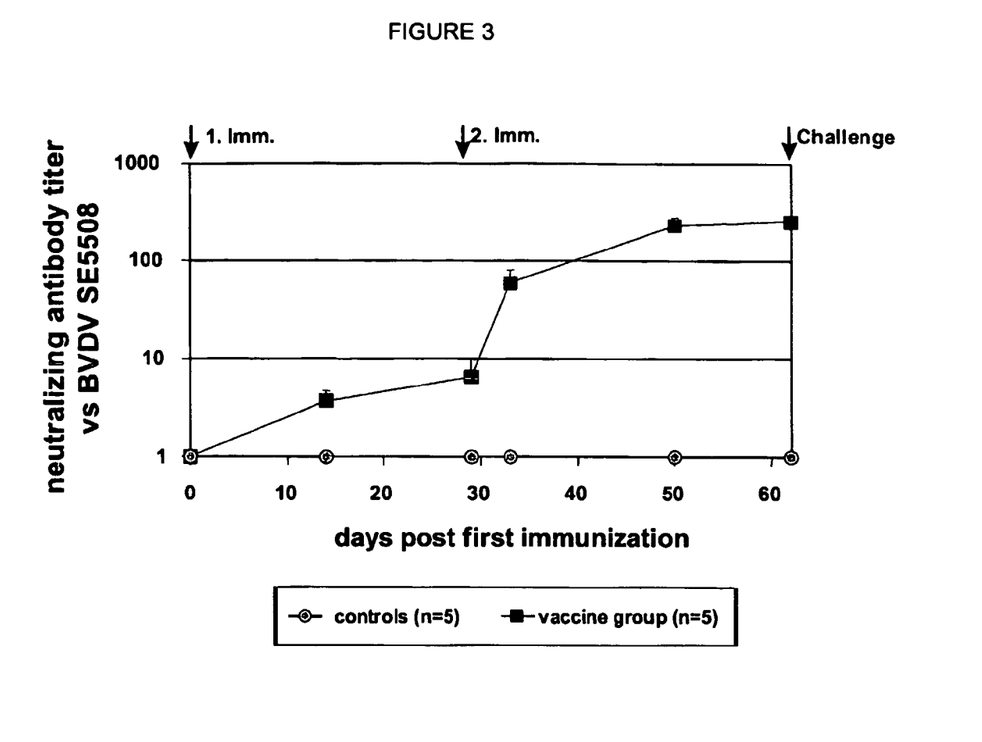

At the time of challenge infection (day 62 after the first immunization) all vaccinated animals had neutralizing titers against the BVDV genotype 1 challenge strain of 1:256 or more than 1:256 (FIG. 3).

Virus Isolation from Blood Leukocytes and Nasal Swabs after Immunization

No replicating BVDV could be isolated in any of the animals after inoculation of NCP7_ΔC_trans. All virus detection assays with blood leukocytes and nasal swabs using KOP-R cells scored negative (Table 4).

Figure 4:
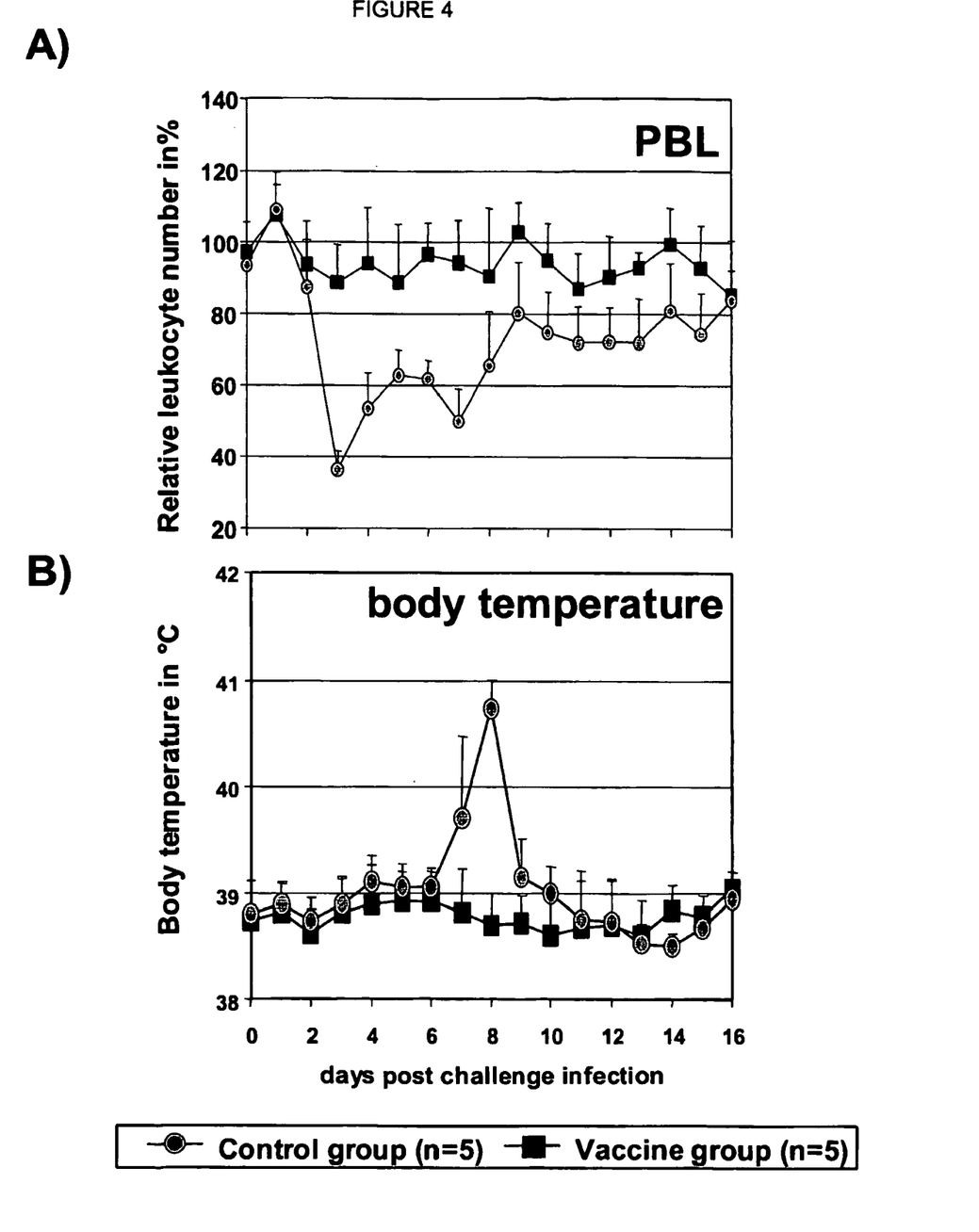

Clinical score, virus isolation, and BVDV antigen detection after challenge infection After challenge infection, neither clinical signs of infection, nor leukopenia, nor fever could be detected in any of the animals vaccinated with trans-complemented replicons (FIGS. 4a and b). In contrast, most of the naïve control animals developed clinical signs of a BVDV infection with respiratory symptoms (nasal discharge, coughing) and depression (data not shown). In all control animals a marked leukopenia between days 3 and 8 as well as high body temperatures of more than 40° C. could be observed post challenge infection (p. chall.) (FIGS. 4a and b).

Figure 5:
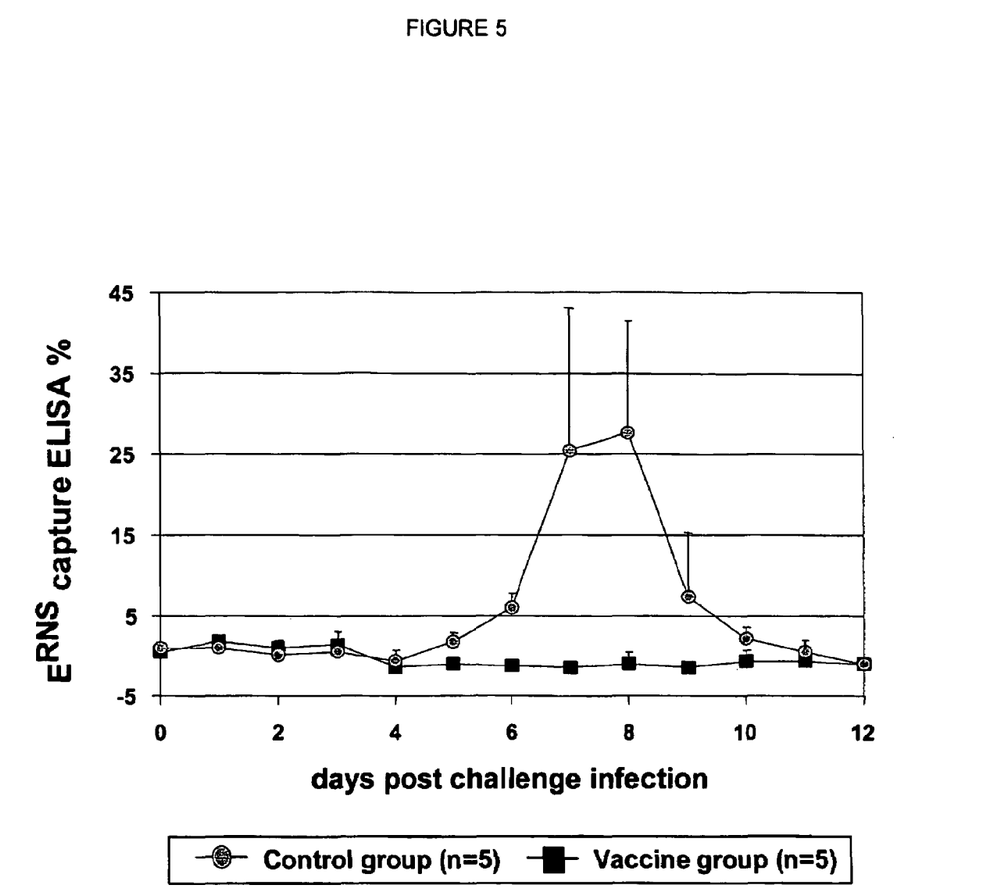

BVDV challenge virus was isolated from blood leukocytes and from nasal swabs of all control animals between days 2 and 10 p. chall. (Table 5). However, no BVDV could be isolated from blood leukocytes and nasal swabs of vaccinated cattle (Table 5). In addition, $E^{RNS}$ antigen detection with a commercial $E^{RNS}$ capture ELISA was negative for all vaccinated animals p. chall., but elevated ELISA values were determined for all animals of the control group between days 5 and 9 (FIG. 5) and three from the five control cattle scored positive with an ELISA value of more than 35% (data not shown).

Serology after Challenge Infection

After challenge infection, all control animals scored positive in the ELISA systems (FIGS. 2a and b) and the neutralization assay (data not shown). BVDV antibodies could be detected from day 14 p. chall. (FIGS. 2a and b). In the vaccinated group, a marked booster effect could be detected with the indirect ELISA (mean values from 0.8 at day 0 p. chall. to 1.9 at day 28 p. chall.), but not with the NS3-blocking ELISA (FIGS. 2a and b).

Discussion

All vaccinated animals remained healthy after inoculation of NCP7_ΔC_trans. No clinical symptoms could be observed, and neither fever nor leukopenia were detected. Following vaccination, no BVDV could be re-isolated from nasal swabs and blood leukocytes. Taken together, occurrence of a revertant NCP7-like virus can be excluded. We therefore conclude, that NCP7_ΔC_trans is apathogenic for cattle and acts like defective in second cycle virions (DISC) or replication incompetent "pseudovirions".

All control animals remained BVDV antibody negative until challenge infection. In contrast, all vaccinated animals developed NS3-specific antibodies after the first immunization, and scored positive in an indirect BVDV antibody ELISA after booster vaccination with NCP7_ΔC_trans.

Following challenge infection with a genotype 1 BVDV, all control animals had a marked leukopenia and fever. In addition, some of the controls developed respiratory symptoms and were depressed for several days. In contrast, none of the vaccinated animals developed any clinical signs, or leukopenia, or fever after challenge infection. In addition, challenge virus was re-isolated from all control animals for several days from blood leukocytes and nasal swabs. However, no BVDV could be isolated from any of the vaccinated animals. We therefore conclude, that immunization with NCP7_ΔC_trans provides complete protection from BVDV clinical signs, viremia and virus shedding.

TABLE 4

Virus isolation from blood leukocytes and nasal swabs following immunization with NCP7_ΔC_trans

| Animal No. | days post first immunization | | | | | | | | | | | days post second immunization | | | | | | | | | | |
|---|---|---|---|---|---|---|---|---|---|---|---|---|---|---|---|---|---|---|---|---|---|---|
| | 0 | 1 | 2 | 3 | 4 | 5 | 6 | 7 | 8 | 9 | 10 | 29 | 30 | 31 | 32 | 33 | 34 | 35 | 36 | 37 | 38 | 39 |
| 173 | 0[a]/0[b] | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| 537 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| 554 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| 758 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| 977 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |

[a] number of positive inoculations with $1 \times 10^6$ leukocytes (2 inoculations per sample; no positive samples = white, 1 positive sample = light grey, 2 positive samples = dark grey)
[b] number of positive inoculations with 10 mg nasal secretion (2 inoculations per sample; no positive samples = white, 1 positive sample = light grey, 2 positive samples = dark grey)

TABLE 5

Virus isolation from blood leukocytes and nasal swabs following challenge infection with BVDV SE5508

| | animal | days post challenge infection (dpc) | | | | | | | | | | | | | | |
|---|---|---|---|---|---|---|---|---|---|---|---|---|---|---|---|---|
| | | 0 | 1 | 2 | 3 | 4 | 5 | 6 | 7 | 8 | 9 | 10 | 11 | 12 | 13 | 14 |
| vaccinated | 173 | 0[a]/0[b] | 0/0 | 0/0 | 0/0 | 0/0 | 0/0 | 0/0 | 0/0 | 0/0 | 0/0 | 0/0 | 0/0 | 0/0 | 0/0 | 0/0 |
| | 554 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| | 537 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| | 758 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| | 977 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| controls | 97 | 0/0 | 0/0 | 0/0 | | | | | | | | 0/0 | 0/0 | 0/0 | 0/0 | 0/0 |
| | 99 | 0/0 | 0/0 | 0/0 | | | | | | | | 0/0 | 0/0 | 0/0 | 0/0 | 0/0 |
| | 172 | 0/0 | 0/0 | 0/0 | 0/0 | | | | | | | 0/0 | 0/0 | 0/0 | 0/0 | 0/0 |
| | 610 | 0/0 | 0/0 | 0/0 | | | | | | | | 0/0 | 0/0 | 0/0 | 0/0 | 0/0 |
| | 611 | 0/0 | 0/0 | | | | | | | | | 0/0 | 0/0 | 0/0 | 0/0 | 0/0 |

[a] number of positive inoculations with $1 \times 10^6$ leukocytes (2 inoculations per sample; no positive samples = white, 1 positive sample = light grey, 2 positive samples = dark grey)
[b] number of positive inoculations with 10 mg nasal secretion (2 inoculations per sample; no positive samples = white, 1 positive sample = light grey, 2 positive samples = dark grey)

The invention claimed is:

1. A replicon of a pestivirus which is incapable of expressing one or more structural proteins of the virus, characterized in that said replicon expresses all structural proteins of a pestivirus except for a functional C protein, but wherein the coding sequences encoding a signal sequence within the C protein essential for post translational processing are retained or replaced by a coding sequence encoding analogous signal sequences from another pestiviral species.

2. The replicon according to claim 1, characterized in that at least part of the coding sequence of the C protein has been deleted from said replicon.

3. The replicon according to claim 1, characterized in that said replicon is of a Bovine Viral Diarrhea Virus (BVDV).

4. The replicon according to claim 3, characterized in that the coding region encoding amino acid positions 201-243 of a BVDV strain NCP-7 polyprotein have been deleted.

5. An infectious viral particle of pestivirus, characterized in that it contains a replicon according to claim 1.

6. A method for the production of infectious viral particles of a pestivirus, characterized in that said method comprises the following steps:
   a. providing cells that are permissive for the pestivirus and express pestiviral C protein,
   b. transfecting said cells with in-vitro transcribed RNA of a replicon according to claim 1,
   c. culturing transfected cells obtained in step b,
   d. harvesting the viral particles from the cultured cells.

7. The method according to claim 6, characterized in that said pestivirus is BVDV.

8. The method according to claim 7, characterized in that said cells express the C protein of BVDV.

9. A vaccine containing infectious viral particles according to claim 5 and a pharmaceutically acceptable carrier.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Bovine Viral Diarrhea virus

<400> SEQUENCE: 1
gtcctaggta cccctgggca                                          20

<210> SEQ ID NO 2
<211> LENGTH: 33
<212> TYPE: DNA
<213> ORGANISM: Bovine Viral Diarrhea virus

<400> SEQUENCE: 2
tctaggtacc tctctgactc cttaggtgtt atc                            33

<210> SEQ ID NO 3
<211> LENGTH: 31
<212> TYPE: DNA
<213> ORGANISM: Bovine Viral Diarrhea virus

<400> SEQUENCE: 3

```
gagaggtacc ctcaagagtc gcgcaagaaa c                              31

<210> SEQ ID NO 4
<211> LENGTH: 20
<212> TYPE: DNA
<213> ORGANISM: Bovine Viral Diarrhea virus

<400> SEQUENCE: 4
gtcctaggta cccctgggca                                           20

<210> SEQ ID NO 5
<211> LENGTH: 21
<212> TYPE: DNA
<213> ORGANISM: Bovine Viral Diarrhea virus

<400> SEQUENCE: 5
aagcctcgag atgccacgtg g                                         21

<210> SEQ ID NO 6
<211> LENGTH: 32
<212> TYPE: DNA
<213> ORGANISM: Bovine Viral Diarrhea virus

<400> SEQUENCE: 6
tcaggtaccg tgcatatgcc ccaaaccatg tc                             32

<210> SEQ ID NO 7
<211> LENGTH: 33
<212> TYPE: DNA
<213> ORGANISM: Bovine Viral Diarrhea virus

<400> SEQUENCE: 7
caacggtacc gaatttggac cgctgctaca acc                            33

<210> SEQ ID NO 8
<211> LENGTH: 21
<212> TYPE: DNA
<213> ORGANISM: Bovine Viral Diarrhea virus

<400> SEQUENCE: 8
aagcctcgag atgccacgtg g                                         21
```